United States Patent [19]

Shapiro et al.

[11] Patent Number: 5,300,430

[45] Date of Patent: Apr. 5, 1994

[54] BIOCATALYTIC PROCESS FOR THE PRODUCTION OF L-(—)-CARNITINE FROM CROTONOBETAINE AND STRAINS OF PROTEUS FOR USE IN SAID PROCESS

[75] Inventors: Stuart Shapiro, Zürich, Switzerland; Manrico Bernardini, Rome, Italy; Charles J. Sih, Madison, Wis.

[73] Assignee: Sigma-Tau Industrie Farmaceutiche Riunite S.p.A., Rome, Italy

[21] Appl. No.: 1,403

[22] Filed: Jan. 7, 1993

Related U.S. Application Data

[63] Continuation of Ser. No. 699,599, May 14, 1991, abandoned.

[30] Foreign Application Priority Data

May 14, 1990 [IT] Italy ............................... 47953 A/90

[51] Int. Cl.$^5$ ......................... C12P 13/00; C12N 1/20
[52] U.S. Cl. ................................. 435/128; 435/252.1; 435/280; 435/873
[58] Field of Search ............ 435/128, 228, 280, 252.1, 435/873

[56] References Cited

U.S. PATENT DOCUMENTS

| | | | |
|---|---|---|---|
| 4,650,759 | 3/1987 | Yokozeki et al. | 435/128 |
| 4,906,568 | 3/1990 | Jung et al. | 435/128 |

OTHER PUBLICATIONS

Sum et al., "Synthesis of L(—)-carnitine by Hydration of Crotonobetaine by Interobacteria," *Appl. Microbiol. Biotechnol.*:27 pp. 538–544, 1988.

*Primary Examiner*—Marian Knode
*Attorney, Agent, or Firm*—Oblon, Spivak, McClelland, Maier & Neustadt

[57] ABSTRACT

A process is described for stereospecifically hydrating crotonobetaine to L-(—)-carnitine via the action of an enzyme produced by four new strains of *Proteus mirabilis* (NRRL B-18480, NRRL B-18481, NRRL B-18482, and NRRL B-18483) in biotransformation media containing from 10 to 12% (w/v) crotonobetaine inner salt.

9 Claims, No Drawings

BIOCATALYTIC PROCESS FOR THE PRODUCTION OF L-(−)-CARNITINE FROM CROTONOBETAINE AND STRAINS OF PROTEUS FOR USE IN SAID PROCESS

This application is a continuation, of Ser. No. 07/699,599, filed on May 14, 1991, now abandoned.

The present invention relates to a process for manufacturing L-(−)-carnitine (2) from crotonobetaine (1) via the action of an enzyme produced by a microorganism, this enzyme catalyzing the stereospecific hydration of crotonobetaine to L-(−)-carnitine.

The present invention also relates to novel Proteeae strains suitable for use in this process.

As known, carnitine contains a single centre of asymmetry and therefore exists as two enantiomorphs, designated D-(+)-carnitine and L-(−)-carnitine. Of these, only L-(−)-carnitine is found in living organisms, where it functions as a vehicle for transporting fatty acids across mitochondrial membranes. Whilst L-(−)-carnitine is the physiologically-active enantiomer, for some years racemic DL-carnitine had been used as a therapeutic agent. It is now recognised, however, that D-(+)-carnitine is a competitive inhibitor of carnitine acyltransferases, and that it can diminish the level of L-(−)-carnitine in myocardium and skeletal muscle.

It is therefore essential that only L-(−)-carnitine be administered to patients undergoing haemodialysis treatment or treatment for cardiac or lipid metabolism disorders.

Various chemical procedures have been proposed for the industrial-scale production of carnitine. These procedures are not stereospecific, leading to racemic mixtures of D-(+)- and L-(−)-isomers. It thus becomes necessary to apply methods of resolution in order to separate the enantiomeric constituents of the racemate. The aforementioned synthetic chemical procedures are complex and costly, and in all cases result in the production of equimolar quantities of D-(+)-carnitine and L-(−)-carnitine.

Several microbiological methods have recently been proposed for producing L-(−)-carnitine, either de novo from common fermentation ingredients or via a stereospecific transformation of achiral betaine derivatives. Regarding the former methods, Japanese patent 71567/1984 (TAKEDA) describes the elaboration of L-(−)-carnitine by the mould *Emericella quadrilineata* when the organism is cultivated in a complex medium. Most of the latter procedures are predicted upon the stereospecific hydration of crotonobetaine to L-(−)-carnitine, and differ principally by virtue of the particular microorganism employed to accomplish the biotransformation of interest.

Most of the organism described in the relevant patent literature belong to the family Enterobacteriaceae [e.g., EP 121,444 (HAMARI), EP 122,799 (AJINOMOTO), DDRP 221,905 (KARL-MARX-UNIVERSITAT), JP Application 61/234788 (SEITETSU)], although non-enterobacteria have also been employed [e.g., EP 158,194 and EP 195,944 (LONZA) which utilise strains of *Achromobacter xylosoxydans*, and JP Application 60/275181 (Biol K. K. & CHO KASEHIN K. K.) for which optimal results were reported using the mould *Penicillium citrinum*].

Substances other than crotonobetaine that have been tried as precursors for the microbial production of L-(−)-carnitine include 3-deydrocarnitine [e.g., JP 272086/1987 (AJINOMOTO)] and carnitine nitrile [EP 319,344 (KYOWA HAKKO KOGYO)].

However, the microbiological procedures proposed to date have not proven practicable for manufacturing L-(−)-carnitine on an industrial scale for one or more of the following reasons:

(i) the yield of L-(−)-carnitine is extremely low;
(i) the yield of L-(−)-carnitine is extremely low;
(ii) the precursor substrate is extremely unstable;
(iii) the microorganisms must be cultivated in a costly nutritive medium;
(iv) the micoorganisms can only tolerate low concentrations [up to 2-3% (w/v)] of crotonobetaine;
(v) side reactions, such as the reduction of crotonobetaine to gammabutyrobetaine or the oxidation of L-(−)-carnitine to 3-dehydrocarnitine, reduce the final yield of L-(−)-carnitine.

The crotonobetaine used in the procedures described below consisted of ca. 89% (w/w) crotonobetaine inner salt (desalinated crotonobetaine)+ca. 11% (w/w) water (determined using Karl Fischer reagent), corresponding to approximately one molecule of water per molecule of crotonobetaine. Consequently, this substrate shall henceforth be referred to as "crotonobetaine monohydrate", although "monohydrate" is not intended to imply a definitive structural relationship between crotonobetaine and water.

Elsewhere, when the term "crotonobetaine inner salt" is used, it refers to 100% pure crotonobetaine inner salt (anhydrous desalinated crotonobetaine).

Four new strains of *Proteus mirabilis*, capable of hydrating crotonobetaine to L-(−)-carnitine on biotransformation media wherein the concentration of crotonobetaine inner salt is about 10-12% (w/v), were isolated and biotyped (see below). These new strains do not require expensive nutrients or additives for either growth or biotransformation; rather, both cell growth and biotransformation can be achieved using simple, inexpensive media. Within the limits of detectability of the analytical methods employed the new strains of *P. mirabilis* of the present invention do not catalyse side reactions, such as those indicated in the aforecited point (v), that reduce the final output of L-(−)-carnitine.

Four *P. mirabilis* isolates were found capable of converting 12% (w/v) crotonobetaine monohydrate (744.4 mM) to L-(−)-carnitine in molar yields exceeding 40%.

The four *P. mirabilis* isolates (designated in-house as Sigma-Tau SP237 subclone NACit I1, Sigma-Tau BT 1IV, Sigma-Tau GP 1AVI, and Sigma-Tau R 2 AIX) were deposited on Apr. 21, 1989 with the Agricultural Research Service Culture Collection, Northern Regional Research Centre, United States Department of Agriculture, 1815 North University Street, Peoria, Ill. 61604 U.S.A., and were assigned the codes NRRL B-18480, NRRL B-18481, NRRL B-18482, and NRRL B-18483, respectively, by the Agricultural Research Service. The isolation method and morphological, and physiological/biochemical properties of the four strains are described below.

(i) Proteus mirabilis NRRL B-18480 (Sigma-Tau SP237 subclone NACit I1).

The organism was originally recognised morphologically as a contaminant on a plate of Acinetobacter lwoffii. The organism was subsequently purified using a medium (henceforth referred to as NACit+cb) consisting of nutrient broth+0.8% ($^w$/v) sodium chloride+0.5% ($^w$/v) citric acid monohydrate+1.5% ($^w$/v)

crotonobetaine monohydrate+2% agar, pH adjusted to 6.8 with potassium hydroxide.

The organism was maintained by daily transfer (37° C.) on NACit+cb; it was typed by the American Type Culture Collection (ATCC) (Rockville, Maryland, U.S.A.), and by the Industrial Microbiology Laboratories at Sigma-Tau Industrie Farmaceutiche Riunite S.p.A. (Pomezia, Italy) using morphological examination in conjunction with API 20 E (version C), API ZYM (version B), and API 50 CHE (version D) strips (API System S. A., Montalieu-Vercieu, France), and other biochemical/physiological tests as deemed necessary.

Morphological Properties
Gram stain: negative
Shape: bacillus
Dimensions: $0.9 \times 4\mu$
Flagella: peritrichous
Motility: present, with swarming
Chromogenesis: negative
Sporulation: negative Physiological/Biochemical Properties
Requirement for $>CO_2$: negative
Requirement for $\geq 0.5\%$ NaCl: negative
Voges-Proskauer (room temperature): weak
Voges-Proskauer (37° C.): doubtful
Methyl red: positive
Production of $H_2S$ (triple sugar iron agar): negative
Growth in Simmons citrate medium: negative
Utilisation of citrate: negative
Utilisation of L-tartrate: negative
Utilisation of mucate: negative
Growth on acetate as sole carbon source: negative
Growth on malonate as sole carbon source: negative
Growth on MacConkey agar: positive
Liquefaction of gelatine: negative
Amino acid auxotrophy: L-histidine
Pectin hydrolysis: negative
Acid phosphatase (naphthol AS-BI phosphate, pH 5.4): negative
Acid phosphatase ($\beta$-naphthyl phosphate, pH 5.4): positive
Alkaline phosphatase ($\beta$-naphthyl phosphate, pH 8.5): positive
Esterase ($\beta$-naphthyl butyrate): negative
Esterase ($\beta$-naphthyl caprylate): negative
Lipase ($\beta$-naphthyl myristate): negative
Hydrolysis of Tween® 20: positive
Hydrolysis of Tween® 80: negative
Arginine dihydrolase: negative
Arginine utilisation (Møller's medium): negative
Ornithine decarboxylase: negative
Lysine decarboxylase: negative
Production of indole: negative
Tryptophane deaminase: positive (weak)
Phenylalanine deaminase: positive
Urease: positive
Trypsin: negative
Chymotrypsin: negative
Cystine arylamidase: negative
Leucine arylamidase: positive
Valine arylamidase: negative
Catalase: positive
Oxidase: negative
Reduction of nitrate to nitrite: positive
Growth in the presence of KCN: positive
O-F Glucose, oxidative: positive
O-F Glucose, fermentative: positive $\alpha$-Galactosidase: negative
$\beta$-Galactosidase: negative
$\beta$-Glucuronidase: negative
$\alpha$-Glucosidase: negative
$\beta$-Glucosidase: negative
N-Acetyl-$\beta$-glucosaminidase: negative
$\alpha$-Fucosidase: negative
$\alpha$-Mannosidase: negative

| Production of Acid and Gas from Carbohydrates (24 h, 37° C.) | | |
|---|---|---|
| Carbohydrate* | Acid | Gas |
| meso-adonitol | − | − |
| aesculin | − | − |
| amygdalin | − | − |
| D-arabinose | +(weak) | − |
| L-arabinose | − | − |
| D-arabitol | − | − |
| L-arabitol | − | − |
| arbutin | − | − |
| cellobiose | − | − |
| meso-dulcitol | − | − |
| meso-erythritol | − | − |
| fructose | − | − |
| D-fucose | − | − |
| L-fucose | − | − |
| galactose | + | − |
| gentiobiose | − | − |
| glucose | + | − |
| $\alpha$-methyl glucoside | − | − |
| gluconate | + | − |
| 2-ketogluconate | − | − |
| 5-ketogluconate | − | − |
| N-acetylglucosamine | + | − |
| glycerol | +(weak) | − |
| glycogen | − | − |
| myo-inositol | − | − |
| inulin | − | − |
| lactose | − | − |
| lyxose | − | − |
| maltose | − | − |
| mannitol | − | − |
| mannose | − | − |
| $\alpha$-methyl mannoside | − | − |
| melezitose | − | − |
| melibiose | − | − |
| raffinose | − | − |
| L-rhamnose | − | − |
| ribose | + | − |
| salicin | − | − |
| sorbitol | − | − |
| L-sorbose | − | − |
| starch | − | − |
| sucrose | +(weak) | − |
| tagatose | − | − |
| trehalose | + | − |
| turanose | − | − |
| meso-xylitol | − | − |
| D-xylose | − | − |
| L-xylose | − | − |
| $\beta$-methyl D-xylose | − | − |

*Unless otherwise indicated, all asymmetric carbohydrates used in these tests were of the D-configuration.

Antibiotic Sensitivities

Antibiogrammes were obtained on Mueller-Hinton agar [Mueller, J. H., and Hinton, J., "A protein-free medium for primary isolation of the gonococcus and meningococcus", Proc. Soc. Exp. Biol. Med., 48:330 (1941)] supplemented with 0.15% starch [Olsen, M. A., and Scott, W. J., "Influence of starch in media used for the detection of heated bacterial spores", Nature, 157:337 (1946)] (14 h, 37° C.), using Oxoid antibiotic susceptibility discs in accordance with the Kirby-Bauer procedure [Bauer, A. W., Kirby, W. M. M., Sherris, K. C., and Turck, M., "Antibiotic susceptibility testing by a standardized single disk method", *Amer. J. Clin. Pathol.*, 45:493 (1966)].

| Antibiotic (amount) | Diameter (mm) of inhibition zone | Interpretation |
|---|---|---|
| amikacin (30 μg) | 17 | susceptible |
| ampicillin (10 μg) | 23 | susceptible |
| benzylpencillin (10 IU) | 22 | susceptible |
| cefuroxime (30 μg) | 28 | susceptible |
| cephalothin (30 μg) | 18 | susceptible |
| chloramphenicol (30 μg) | 20 | susceptible |
| colistin (10 μg) | 11 | susceptible |
| gentamicin (10 μg) | 17 | susceptible |

One the basis of these results, the isolate corresponds to a strain of *Proteus mirabilis* according to the classification scheme of the ATCC; moreover, according to the ATCC, *Proteus mirabilis* NRRL B-18480 (Sigma-Tau SP237 subclone NACit I1) is unique and does not correspond to any other organism in their culture collection.

It has been observed that extensively-purified single clones of *P. mirabilis* NRRL B-18480 that are urease-positive (ure+) can give rise to urease-negative (ure−) clones at a low frequency; the morphological-physiological/biochemical profile and the antibiogramme of these ure− variants are otherwise identical to those of their ure+ progenitors [cf. Farmer, J. J., III, Hickman, F. W., Brenner, D. J., Schreiber, M., and Rickenbach, D. G., "Unusual Enterobacteriaceae: '*Proteus rettgeri*' that 'change' into *Providencia stuartii*", *J. Clin. Microbiol.*, 6:373 (1977); Collins, C. M., and Falkow, S., "Genetic analysis of an *Escherichia coli* urease locus: evidence of DNA rearrangement", *J. Bacteriol.*, 170:1041 (1988)]. Moreover, the capacity of the ure− variants to convert crotonobetaine to L-(−)-carnitine is unchanged. The reverse phenotypic transformation, i.e., the spontaneous appearance of a ure+ strain of *P. mirabilis* NRRL B-18480 from a ure− antecedent, has not been observed by us (cf. Lewis, A. D., and Rosen, I. G., "Characterization of a *Proteus rettgeri* that transfers genes for urease production and lactose fermentation", *American Society for Microbiology Annual Meeting*, 1973, Abstract G 218).

(ii) Proteus mirabilis NRRL B-18482 (Sigma-Tau GP 1AVI).

The organism was isolated from faeces obtained from a guinea-pig in the animal collection of Sigma-Tau Industrie Farmaceutiche Riunite S.p.A.

Fresh faecal matter (0.5–1.0 g) was incubated for 24 h without agitation in 4 mL of sterile brain-heart infusion (BHI) (Difco) +1.5% (w/v) crotonobetaine monohydrate (pII 6.8, 37° C.). Loopfuls of broth were taken from just below the meniscus and streaked onto plates of the medium described by Xilinas, M. E., Papavissiliou, J. T., and Legakis, N.J. ["Selective medium for growth of Proteus, *J. Clin. Microbiol.*, 2: 459 (1975)], hereafter referred to as "Greek agar". After 48 h at 37° C., single colonies were picked and purified by repeated restreaking of single clones on plates of Greek agar +1.5% (w/v) crotonobetaine monohydrate (pH 6.8, 37° C., 48 h) and MacConkey agar CS (Difco) +1.5% (w/v) crotonobetaine monohydrate (pH 6.8, 37° C., 44 h).

The organism was maintained by daily transfer (37° C.) on Greek agar +1.5% (w/v) crotonobetaine monohydrate. It was typed in the Industrial Microbiology Laboratories at Sigma-Tau Industrie Farmaceutiche Riunite S.p.A. using morphological examination in conjunction with the API 20 E, API ZYM, and API 50 CHE strips, and other biochemical/physiological tests as deemed necessary.

Morphological Properties
Gram stain: negative
Shape: bacillus
Dimensions: $0.8 \times 2\mu$
Motility (NACit +cb; BHI +1.5% (w/v) crotonobetaine monohydrate +2% agar, pH 6.8); present, with swarming
Chromogenesis: negative
Sporulation: negative Physiological/Biochemical Properties (37° C.)
Requirement for >$CO_2$: negative
Voges-Proskauer: weak
Production of $H_2S$ (triple sugar iron agar): positive
Growth in Simmons citrate medium: negative
Growth on MacConkey agar: positive
Liquefaction of gelatine: negative
Amino acid auxotrophy: none
Acid phosphatase (naphthol AS-BI phosphate, pH 5.4): positive (weak)
Acid phosphatase (β-naphthyl phosphate, pH 5.4): positive
Alkaline phosphatase (β-naphthyl phosphate, pH 8.5): positive
Esterase (β-naphthyl butyrate): positive (weak)
Esterase (β-naphthyl caprylate): negative
Lipase (β-naphthyl myristate): negative
Arginine dihydrolase: negative
Ornithine decarboxylase: positive
Lysine decarboxylase: negative
Production of indole: negative
Tryptophane deaminase: positive
Phenylalanine deaminase: positive
Urease: positive
Trypsin: negative
Chymotrypsin: negative
Cystine arylamidase: negative
Leucine arylamidase: positive
Valine arylamidase: negative
Oxidase: negative
O-F glucose, oxidative: positive
O-F glucose, fementative: positive
α-Galactosidase: negative
β-Galactosidase: negative
β-Glucuronidase: negative
α-Glucosidase: negative
β-Glucosidase: negative
N-Acetyl-β-glucosaminidase: negative
α-Fucosidase: negative
α-Mannosidase: negative

| Production of Acid and Gas from Carbohydrates (24 h, 37° C.) | | |
|---|---|---|
| Carbohydrate* | Acid | Gas |
| meso-adonitol | − | − |
| aesculin | − | − |
| amygdalin | | |
| D-arabinose | +(weak) | − |
| L-arabinose | − | − |
| D-arabitol | − | − |
| L-arabitol | − | − |
| arbutin | | |
| cellobiose | − | − |
| meso-dulcitol | − | − |
| meso-erythritol | − | − |
| fructose | | |
| D-fucose | − | − |
| L-fucose | − | − |

| Production of Acid and Gas from Carbohydrates (24 h, 37° C.) | | |
|---|---|---|
| Carbohydrate* | Acid | Gas |
| galactose | + | − |
| gentiobiose | − | − |
| glucose | + | − |
| α-methyl glucoside | − | − |
| gluconate | + | − |
| 2-ketogluconate | +(weak) | − |
| 5-ketogluconate | − | − |
| N-acetylglucosamine | + | − |
| glycerol | +(weak) | − |
| glycogen | − | − |
| myo-inositol | − | − |
| inulin | − | − |
| lactose | − | − |
| lyxose | − | − |
| maltose | − | − |
| mannitol | − | − |
| mannose | − | − |
| α-methyl mannoside | − | − |
| melezitose | − | − |
| melibiose | − | − |
| raffinose | − | − |
| L-rhamnose | − | − |
| ribose | + | − |
| salicin | − | − |
| sorbitol | − | − |
| L-sorbose | − | − |
| starch | − | − |
| sucrose | − | − |
| tagatose | − | − |
| trehalose | + | − |
| turanose | − | − |
| meso-xylitol | − | − |
| D-xylose | + | − |
| L-xylose | − | − |
| β-methyl D-xylose | − | − |

*Unless otherwise indicated, all asymmetric carbohydrates used in these tests were of the D-configuration.

Antibiotic Sensitivities

Antibiogrammes were obtained exactly as described for *P. mirabilis* NRRL B-18480 (Sigma-Tau SP237 subclone NACit I1).

| Antibiotic (amount) | Diameter (mm) of inhibition zone | Interpretation |
|---|---|---|
| amikacin (30 μg) | 17 | susceptible |
| ampicillin (10 μg) | 22 | susceptible |
| benzylpencillin (10 IU) | 18 | intermediate |
| cefuroxime (30 μg) | 22 | susceptible |
| cephalothin (30 μg) | 21 | susceptible |
| chloramphenicol (30 μg) | 20 | susceptible |
| colistin (10 μg) | / | resistant |
| gentamicin (10 μg) | 17 | susceptible |

On the basis of these results, the isolated organism corresponds to a strain of *Proteus mirabilis* according to the classification scheme of the API system.

(iii) *Proteus mirabilis* NRRL B-1848[1](Sigma-Tau BT 1[IV]).

The organism was isolated from faeces obtained from a rabbit in the animal collection of Sigma-Tau Industrie Farmaceutiche Riunite S. p. A. exactly as described for *Proteus mirabilis* NRRL B-1848[2] (Sigma-Tau [GP] 1AVI). The organism was maintained by daily transfer (37° C.) on Greek agar +1.5% (w/v) crotonobetaine monohydrate. It was typed in the Industrial Microbiology Laboratories of Sigma-Tau Industrie Farmaceutiche Riunite S. p. A. using morphological examination in conjunction with the API 20 E, APIZYM, and API 50 CHE strips, and other biochemical/physiological tests as deemed necessary.

Morphological Properties

Gram stain: negative
Shape: bacillus
Dimensions: $0.8 \times 2\mu$
Motility (NACit+cb; BHI +1.5% (w/v) crotonobetaine monohydrate +2% agar, pH 6.8): present, with swarming
Chromogenesis: negative
Sporulation: negative Physiological/Biochemical Properties (37° C.)

Requirement for $>CO_2$: negative
Voges-Proskauer: negative
Production of $H_2S$ (triple sugar iron agar): positive
Growth in Simmons citrate medium: negative
Growth on MacConkey agar: positive
Liquefaction of gelatine: positive
Amino acid auxotrophy: none
Acid phosphatase (naphthol AS-BI phosphate, pH 5.4): positive (weak)
Acid phosphatase (β-naphthyl phosphate, pH 5.4): positive
Alkaline phosphatase (β-naphthyl phosphate, pH 8.5): positive
Esterase (β-naphthyl butyrate): positive (weak)
Esterase (β-naphthyl caprylate): negative
Lipase (β-naphthyl myristate): negative
Arginine dihydrolase: negative
Ornithine decarboxylase: positive
Lysine decarboxylase: negative
Production of indole: negative
Tryprophane deaminase: positive
Phenylalanine deaminase: positive
Urease: positive
Trypsin: positive
Chymotrypsin: negative
Cystine arylamidase: negative
Leucine arylamidase: positive
Valine arylamidase: negative
Oxidase: negative
O-F Glucose, oxidative: positive
O-F Glucose, fermentative: positive
α-Galactosidase: negative
β-Galactosidase: negative
β-Glucuronidase: negative
α-Glucosidase: negative
β-Glucosidase: negative
N-Acetyl-β-glucosaminidase: negative
α-Fucosidase: negative
α-Mannosidase: negative

| Production of Acid and Gas from Carbohydrates (24 h, 37° C.) | | |
|---|---|---|
| Carbohydrate* | Acid | Gas |
| meso-adonitol | − | − |
| aesculin | − | − |
| amygdalin | − | − |
| D-arabinose | +(weak) | − |
| L-arabinose | − | − |
| D-arabitol | − | − |
| L-arabitol | − | − |
| arbutin | − | − |
| cellobiose | − | − |
| meso-dulcitol | − | − |
| meso-erythritol | − | − |
| fructose | − | − |
| D-fucose | − | − |

-continued

| Production of Acid and Gas from Carbohydrates (24 h, 37° C.) | | |
|---|---|---|
| Carbohydrate* | Acid | Gas |
| L-fucose | − | − |
| galactose | + | − |
| gentiobiose | − | − |
| glucose | + | − |
| α-methyl glucoside | − | − |
| gluconate | + | − |
| 2-ketogluconate | +(weak) | − |
| 5-ketogluconate | − | − |
| N-acetylglucosamine | + | − |
| glycerol | +(weak) | − |
| glycogen | − | − |
| myo-inositol | − | − |
| inulin | − | − |
| lactose | − | − |
| lyxose | − | − |
| maltose | − | − |
| mannitol | − | − |
| mannose | − | − |
| α-methyl mannoside | − | − |
| melezitose | − | − |
| melibiose | − | − |
| raffinose | − | − |
| L-rhamnose | − | − |
| ribose | + | − |
| salicin | − | − |
| sorbitol | − | − |
| L-sorbose | − | − |
| starch | − | − |
| sucrose | − | − |
| tagatose | − | − |
| trehalose | + | − |
| turanose | − | − |
| meso-xylitol | − | − |
| D-xylose | + | − |
| L-xylose | − | − |
| β-methyl D-xylose | − | − |

*Unless otherwise indicated, all asymmetric carbohydrates used in these tests were of the D-configuration.

Antibiotic Sensitivities

Antibiogrammes were obtained exactly as described for P. mirabilis NRRL B-18480 (Sigma-Tau SP237 subclone NACit I1).

| Antibiotic (amount) | Diameter (mm) of inhibition zone | Interpretation |
|---|---|---|
| amikacin (30 μg) | 17 | susceptible |
| ampicillin (10 μg) | 20 | susceptible |
| benzylpencillin (10 IU) | 16 | intermediate |
| cefuroxime (30 μg) | 20 | susceptible |
| cephalothin (30 μg) | 21 | susceptible |
| chloramphenicol (30 μg) | 18 | susceptible |
| colistin (10 μg) | / | resistant |
| gentamicin (10 μg) | 17 | susceptible |

On the basis of these results, the isolated organism corresponds to a strain of Proteus mirabilis according to the classification scheme of the API system.

(w) Proteus mirabilis B-18483 (Sigma-Tau R 2AIX).

The organism was isolated from faeces obtained from a rat in the animal collection of Sigma-Tau Industrie Farmaceutiche Riunite S.p.A. exactly as described for Proteus mirabilis NRRL B-18482 (Sigma-Tau GP 1AVI). The organism was maintained by daily transfer (37° C.) on Greek agar +1.5% (w/v) crotonobetaine monohydrate. It was typed in the Industrial Microbiology Laboratories of Sigma-Tau Industrie Farmaceutiche Riunite S.p.A. using morphological examination in conjunction with the API 20 E, API ZYM, and API 50 CHE strips, and other biochemical/physiological tests as deemed necessary.

Morphological Properties
Gram stain: negative
Shape: bacillus
Dimensions: $0.8 \times 3\mu$
Motility (NACit+cb; BHI+1.5% (w/v) crotonobetaine monohydrate+2% agar, pH 6.8): present, with swarming
Chromogenesis: negative
Sporulation: negative
  Physiological/Biochemical Properties (37° C.)
Requirement for >$CO_2$: negative
Voges-Proskauer: negative
Production of $H_2S$ (triple sugar iron agar): positive
Growth in Simmons citrate medium: negative
Growth on MacConkey agar: positive
Liquefaction of gelatine: positive
Amino acid auxotrophy: none
Acid phosphatase (naphthol AS-BI phosphate, pH 5.4): negative
Acid phosphatase (β-naphthyl phosphate, pH 5.4): positive
Alkaline phosphatase (β-naphthyl phosphate, pH 8.5): positive
Esterase (β-naphthyl butyrate): positive (weak)
Esterase (β-naphthyl caprylate): negative
Lipase (β-naphthyl myristate): negative
Arginine dihydrolase: negative
Ornithine decarboxylase: positive
Lysine decarboxylase: negative
Production of indole: negative
Tryptophane deaminase: positive
Phenylalanine deaminase: positive
Urease: positive
Trypsin: negative
Chymotrypsin: negative
Cystine arylamidase: negative
Leucine arylamidase: positive
Valine arylamidase: negative
Oxidase: negative
O-F Glucose, oxidative: positive
O-F Glucose, fermentative: positive
α-Galactosidase: negative
β-Galactosidase: negative
β-Glucuronidase: negative
α-Glucosidase: negative
β-Glucosidase: negative
N-Acetyl-β-glucosaminidase: negative
α-Fucosidase: negative
α-Mannosidase: negative

| Production of Acid and Gas from Carbohydrates (24 h, 37° C.) | | |
|---|---|---|
| Carbohydrate* | Acid | Gas |
| meso-adonitol | − | − |
| aesculin | − | − |
| amygdalin | − | − |
| D-arabinose | +(weak) | − |
| L-arabinose | − | − |
| D-arabitol | − | − |
| L-arabitol | − | − |
| arbutin | − | − |
| cellobiose | − | − |
| meso-dulcitol | − | − |
| meso-erythritol | − | − |
| fructose | − | − |
| D-fucose | − | − |
| L-fucose | − | − |
| galactose | + | − |
| gentiobiose | − | − |

-continued

| Production of Acid and Gas from Carbohydrates (24 h, 37° C.) | | |
|---|---|---|
| Carbohydrate* | Acid | Gas |
| glucose | + | − |
| α-methyl glucoside | − | − |
| gluconate | + | − |
| 2-ketogluconate | − | − |
| 5-ketogluconate | − | − |
| N-acetylglucosamine | + | − |
| glycerol | +(weak) | − |
| glycogen | − | − |
| myo-inositol | − | − |
| inulin | − | − |
| lactose | − | − |
| lyxose | − | − |
| maltose | − | − |
| mannitol | − | − |
| mannose | − | − |
| α-methyl mannoside | − | − |
| melezitose | − | − |
| melibiose | − | − |
| raffinose | − | − |
| L-rhamnose | − | − |
| ribose | + | − |
| salicin | − | − |
| sorbitol | − | − |
| L-sorbose | − | − |
| starch | − | − |
| sucrose | − | − |
| tagatose | − | − |
| trehalose | + | − |
| turanose | − | − |
| meso-xylitol | − | − |
| D-xylose | + | − |
| L-xylose | − | − |
| β-methyl D-xylose | − | − |

*Unless otherwise indicated, all asymmetric carbohydrates used in these tests were of the D-configuration.

Antibiotic Sensitivities

Antibiogrammes were obtained exactly as described for *P. mirabilis* NRRL B-18480 (Sigma-Tau SP237 subclone NACit I1).

| Antibiotic (amount) | Diameter (mm) of inhibition zone | Interpretation |
|---|---|---|
| amikacin (30 μg) | >30 | susceptible |
| ampicillin (10 μg) | >30 | susceptible |
| benzylpencillin (10 IU) | 25 | susceptible |
| cefuroxime (30 μg) | >30 | susceptible |
| cephalothin (30 μg) | >30 | susceptible |
| chloramphenicol (30 μg) | / | resistant |
| colistin (10 μg) | / | resistant |
| gentamicin (10 μg) | >30 | susceptible |

On the basis of these results, the isolated organism corresponds to a strain of *Proteus mirabilis* according to the classification scheme of the API system.

Comparative Biotransformation Data for the Synthesis of L-(−)-Carnittine from Crotonobetaine by *Proteus mirabilis* Isolates in Shaken Flasks

*Proteus mirabilis* NRRL B-18480 (Sigma-Tau SP237 subclone NACit I1) was maintained by daily transfer on plates of NACit+cb; incubation temperature, 37° C. *Proteus mirabilis* NRRL B-18481 (Sigma-Tau BT 1IV), *P. mirabilis* NRRL B-18482 (Sigma-Tau GP 1AVI), and *P. mirabilis* NRRL B-18483 (Sigma-Tau R 2AIX) were maintained by daily transfer on plates of Greek agar +1.5% (w/v) crotonobetaine monohydrate, pH 6.8; incubation temperature, 37° C.

Loopfuls of the foregoing strains were inoculated into 250 mL Erlenmeyer flasks, each containing 50 mL of brain-heart infusion +1.5% (w/v) crotonobetaine monohydrate, pH 6.8. The flasks were shaken (200 rpm, 1-inch orbital eccentricity, 37° C.) for 17 h, then the cells were collected by centrifugation (10 min, 12,000×g, 4° C.), and washed once with cold physiological saline (50 mL). Washed cell pellets were resuspended in non-sterile biotransformation medium (50 mL) consisting of 25 mM potassium phosphate +1% (w/v) glycerol +12% (w/v) crotonobetaine monohydrate, pH 6.0. Biotransformation reactions were shaken as above at 33° C. for 96 h; during this period aliquots (100 μL) were withdrawn and assayed enzymically for L-(−)-carnitine by the method of Pearson, D. J. Chase, J. F. A., and Tubbs, P. K. ["The assay of (−)-carnitine and its O-acyl derivatives ", *Meth. Enzymol.*, 9:612 (1966)].

The following results were obtained (corrected for evaporation over the period 0–96 h):

| | mM L-(−)-CARNITINE ACCUMULATED | |
|---|---|---|
| h | *P. mirabilis* NRRL B-18480 (SP237 subclone NACit I1) | *P. mirabilis* NRRL B-18482 (GP 1AVI) |
| 5 | 104 | 80 |
| 24 | 260 | 184 |
| 48 | 285 | 257 |
| 72 | 299 | 286 |
| 96 | 340 | 315 |
| h | *P. mirabilis* NRRL B-18481 (BT 1IV) | *P. mirabilis* NRRL B-18483 (R 2AIX) |
| 5 | 84 | 102 |
| 24 | 229 | 258 |
| 48 | 254 | 295 |
| 72 | 307 | 292 |
| 96 | 311 | 296 |

| | % TURNOVER OF EXOGENOUS CROTONOBETAINE* TO L-(−)-CARNITINE* | |
|---|---|---|
| h | *P. mirabilis* NRRL B-18480 (SP237 subclone NACit I1) | *P. mirabilis* NRRL B-18482 (GP 1AVI) |
| 5 | 14 | 11 |
| 24 | 35 | 25 |
| 48 | 38 | 34 |
| 72 | 40 | 39 |
| 96 | 46 | 42 |
| h | *P. mirabilis* NRRL B-18481 (BT 1IV) | *P. mirabilis* NRRL B-18483 (R 2AIX) |
| 5 | 11 | 14 |
| 24 | 31 | 35 |
| 48 | 35 | 40 |
| 72 | 41 | 39 |
| 96 | 42 | 40 |

*100% = 744.4 mM

Alternative Complex Media Supporting High "Crotonobetaine Hydratase" Activity in *Proteus mirabilis* NRRL B-18480 (Sigma-Tau SP237 subclone NACit I1)

*Proteus mirabilis* NRRL B-18480 (Sigma-Tau SP237 subclone NACit I1) was maintained by daily transfer on plates of NACit +cb; incubation temperature, 37° C. Loopfuls of this strain were inoculated into a 250-mL Erlenmeyer flask containing 50 mL of diverse media:

(a) Brain-heart infusion (Difco) +1.5% (w/v) crotonobetaine monohydrate, pH 6.8.

(b) 0.9% Nutrient broth (Difco) +0.9% yeast extract (Difco) +0.9% Soytone (Difco) +0.2% glucose +0.5% sodium chloride +0.25% dibasic sodium phosphate (anhydrous) +1.5% (w/v) crotonobetaine monohydrate, pH 6.8.

(c) 1.35% Nutrient broth +1.35% Soytone +0.2% glucose +0.5% sodium chloride +0.25% dibasic sodium phosphate (anhydrous) +1.5% (w/v) crotonobetaine monohydrate, pH 6.8.

(d) 1.35% Soytone +1.35% yeast extract +0.2% glucose +0.5% sodium chloride +0.25% dibasic sodium phosphate (anhydrous) +1.5% (w/v) crotonobetaine monohydrate, pH 6.8.

(e) 1.35% Nutrient broth +1.35% yeast extract +0.2% glucose +0.25% sodium chloride +0.25% dibasic sodium phosphate (anhydrous) +1.5% (w/v) crotonobetaine monohydrate, pH 6.8.

(f) 0.9% Nutrient broth +0.9% Soytone +0.9% yeast extract +0.5% sodium chloride +0.25% dibasic sodium phosphate (anhydrous) +1.5% (w/v) crotonobetaine monohydrate, pH 6.8.

(g) 0.9% Nutrient broth +0.9% Soytone +0.9% yeast extract +0.2% glucose +0.25% dibasic sodium phosphate (anhydrous) +1.5% (w/v) crotonobetaine monohydrate, pH 6.8.

(h) 0.9% Nutrient broth +0.9% Soytone +0.9% yeast extract +0.2% glucose +0.5% sodium chloride +1.5% (w/v) crotonobetaine monohydrate, pH 6.8.

(i) Brain-heart infusion, pH 6.8.

The flasks were shaken (200 rpm, 1-inch orbital eccentricity, 37° C.) for 17 h, then the cells from each flask were harvested separately by centrifugation (10 min, 12,000× g, 4° C.), and washed once with cold physiological saline (50 mL). Washed cell pellets were resuspended in non-sterile biotransformation medium (50 mL) consisting of 25 mM potassium phosphate +1% (w/v) glycerol +12% (w/v) crotonobetaine monohydrate, pH 6.0. Biotransformation reaction mixtures were shaken as above at 33° C. for 96 h; during this period aliquots (100 μL) were withdrawn and assayed enzymically for L-(−)-camitine as previously described.

The following results were obtained (corrected for evaporation over the period 0-96 h):

| | mM L-(−)-CARNITINE ACCUMULATED | | | | | | | | |
|---|---|---|---|---|---|---|---|---|---|
| h | (a) | (b) | (c) | (d) | (e) | (f) | (g) | (h) | (i) |
| 5 | 85 | 130 | 80 | 140 | 164 | 91 | 130 | 104 | 18 |
| 24 | 232 | 244 | 173 | 256 | 256 | 232 | 217 | 244 | 71 |
| 48 | 278 | 285 | 243 | 279 | 266 | 272 | 222 | 271 | 113 |
| 72 | 334 | 323 | 255 | 299 | 299 | 317 | 252 | 283 | 125 |
| 96 | 338 | 347 | 268 | 315 | 323 | 323 | 259 | 297 | 129 |

| | % TURNOVER OF EXOGENOUS CROTONOBETAINE* TO L-(−)-CARNITINE* | | | | | | | | |
|---|---|---|---|---|---|---|---|---|---|
| h | (a) | (b) | (c) | (d) | (e) | (f) | (g) | (h) | (i) |
| 5 | 11 | 17 | 11 | 19 | 22 | 12 | 17 | 14 | 2 |
| 24 | 31 | 33 | 23 | 34 | 34 | 31 | 29 | 33 | 10 |
| 48 | 37 | 38 | 33 | 37 | 36 | 37 | 30 | 36 | 15 |
| 72 | 45 | 43 | 34 | 40 | 40 | 43 | 34 | 38 | 17 |
| 96 | 45 | 47 | 36 | 42 | 43 | 43 | 35 | 40 | 17 |

*100% = 744.4 mM

Biotransformation of Crotonobetaine to L-(−)-Carnitine by Proteus mirabilis NRRL B-18480 in a Benchtop Fermentor The biotransformation of crotonobetaine inner salt to L-(−)-carnitine was accomplished using cells of P. mirabilis NRRL B-18480 in a 2-L benchtop fermentor, as follows:

The bacterium was maintained by daily transfer on slants of brain-heart infusion agar (Difco) +1.5% (w/v) crotonobetaine inner salt; incubation temperature, 37° C.

The contents of a 24-h slant were inoculated into a baffled 1000-mL Erlenmeyer flask containing 250 mL of brain-heart infusion (Difco) +1.5% (w/v) crotonobetaine inner salt. The flask was continuously shaken (170 rpm, 2-inch orbital eccentricity, 37° C.) for 6 h, after which time the broth was used to inoculate six second-stage cultures, each containing 250 mL of brain-heart infusion +1.5% (w/v) crotonobetaine inner salt, in baffled 1000-mL Erlenmeyer flasks. These flasks were shaken as described above for ca. 15 h; the cells were then recovered by centrifugation (20 min, 8,500× g, 4° C.) and resuspended in a biotransformation medium (1 L) consisting of 25 mM potassium phosphate +0.5% (w/v) glycerol +10% (w/v) crotonobetaine inner salt. A 2-L Biolafitte fermentor was charged with the cell-containing biotransformation medium and operated for 24 h under the following conditions:

agitation rate: 150 rpm
air flow rate: 1 v/v/m
initial pH: ~6.8
working volume: 1L
temperature: 35° C.

A 10% (w/v) glycerol solution was continuously pumped into the fermentor at a rate of 5 mL/h.

Unreacted crotonobetaine and L-(−)-carnitine concentrations were monitored by high-pressure liquid chromatography (HPLC):

column: 10-μ Partisil SCX, 4 mm×250 mm (PoliConsult Scientifica s.r.l., Rome, Italy)
column temperature: 35° C.
injection volume: 10 μL
mobile phase: 75 mM $KH_2PO_4$-$CH_3CN$ (4:6), pH unadjusted
detector: refractive index
retention times (min): L-(−)-carnitine, 8.52 crotonobetaine, 9.81 gamma-butyrobetaine, 12.08.

At 22 h, the biotransformation medium was collected and filtered.

The filtrate, analyzed enzymically for L-(−)-carnitine as previously described, was found to contain 48.0 mg/mL L-(−)-carnitine and 57.3 mg/mL unreacted crotonobetaine.

Molar turnover of crotonobetaine to L-(−)-carnitine: 43%. Yield of l-(−)-carnitine: 100%.

Isolation of L-(−)-Carnitine From The Biotransformation Fluid.

The filtered biotransformation fluid was successively passed through columns of Amberlite$^R$ ion-exchange resins, viz. IRA-402 basic resin (OH-form) and IRC-50 acid resin ($H^{30}$ form), to remove inorganic cations and anions. The eluate was concentrated in vacuo (50° C.), and the concentrate treated with isobutanol three times to azeotropically lower the water content to 5-10% (w/w).

The resulting mixture was crystallised using 3 parts (w/v) of isobutanol, to yield a precipitate containing 4 parts of L-(−)-carnitine and 1 part of crotonobetaine (w/w) [HPLC]. After three successive crystallisations, a solid consisting of L-(−)-carnitine with >0.5% (w/w) of crotonobetaine HPLC was obtained.

By this procedure, ca. 50% (w/w) of the L-(−)-carnitine present in the biotransformation medium was recovered $[\alpha]^{25} = -31.5°$. The mother liquors were collected and recycled in succeeding biotransformation.

We claim:

1. A microbiological process for producing L-(−)-carnitine that comprises:
   (a) preparing a surface culture on a solid medium of a microorganism capable of steroselectively hydrating crotonobetaine to L-(−)-carnitine;
   (b) preparing a catalytically-active biomass by inoculating a liquid medium containing crotonobetaine with the culture obtained in step (a);
   (c) separating the biomass from the liquid medium;
   (d) incubating the separated biomass in a biotransformation fluid containing at least 10% (w/v) of crotonobetaine inner salt for a time and under conditions sufficient for the production of L-(−)-carnitine, and
   (e) recovering L-(−)-carnitine from the biotransformation fluid, wherein said microorganism is selected from the group consisting of *Proteus mirabilis* NRRL B-18480, *Proteus mirabilis* NRRL B-18481, *Proteus mirabilis* NRRL B-18482, and *Proteus mirabilis* NRRL B-18483.

2. The process of claim 1, wherein the biotransformation medium contains 10-12% (w/v) crotonobetaine inner salt.

3. The process of claim 1, wherein the solid medium of step (a) contains crotonobetaine.

4. The process of claim 1, wherein the separation step (c) is accomplished by centrifugation.

5. The process of claim 1, wherein the separation step (c) is accomplished by ultrafiltration.

6. A biologically pure culture of *Proteus mirabilis* NRRL B-18480 or mutants thereof which retain the ability to produce L-(−)-carnitine from crotonobetaine.

7. A biologically pure culture of *Proteus mirabilis* NRRL B-18481 or mutants thereof which retain the ability to produce L-(−)-carnitine from crotonobetaine.

8. A biologically pure culture of *Proteus mirabilis* NRRL B-18482 or mutants thereof which retain the ability to produce L-(−)-carnitine from crotonobetaine.

9. A biologically pure culture of *Proteus mirabilis* NRRL B-18482 or mutants thereof which retain the ability to produce L-(−)-carnitine from crotonobetaine.

* * * * *